(12) United States Patent
Khandaker et al.

(10) Patent No.: US 10,415,156 B2
(45) Date of Patent: Sep. 17, 2019

(54) METHOD AND APPARATUS FOR CONTROLLED ALIGNMENT AND DEPOSITION OF BRANCHED ELECTROSPUN FIBER

(71) Applicant: UNIVERSITY OF CENTRAL OKLAHOMA, Edmond, OK (US)

(72) Inventors: Morshed Khandaker, Edmond, OK (US); William Paul Snow, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 411 days.

(21) Appl. No.: 14/734,147

(22) Filed: Jun. 9, 2015

(65) Prior Publication Data

US 2016/0047064 A1 Feb. 18, 2016

Related U.S. Application Data

(60) Provisional application No. 62/038,506, filed on Aug. 18, 2014.

(51) Int. Cl.
*D01D 5/00* (2006.01)
*A61C 13/00* (2006.01)

(52) U.S. Cl.
CPC ....... *D01D 5/0084* (2013.01); *A61C 13/0006* (2013.01); *D01D 5/0076* (2013.01); *A61F 2240/001* (2013.01)

(58) Field of Classification Search
CPC ........................................ D01D 5/0061–9984
See application file for complete search history.

(56) References Cited

U.S. PATENT DOCUMENTS

| 692,631 A | 2/1902 | Cooley |
| 1,975,504 A | 10/1934 | Formhals |
| 2,109,333 A | 2/1938 | Formhals |

(Continued)

FOREIGN PATENT DOCUMENTS

| CN | 1687493 A | 10/2005 |
| CN | 1766181 A | 5/2006 |

(Continued)

OTHER PUBLICATIONS

Yarin et al., "Branching in electrospinning of nanofibers", Journal of Applied Physics 98, pp. 064501, 2005, pp. 1-12.

(Continued)

*Primary Examiner* — Dah-Wei D. Yuan
*Assistant Examiner* — Stephen A Kitt
(74) *Attorney, Agent, or Firm* — Berenato & White, LLC

(57) ABSTRACT

A method for separating out a continuous single thread of fiber from many fiber branches and controlling alignment and deposition of said fiber on a substrate, comprising: electrospinning synthetic polymer fiber streams from an electrically charged syringe needle; controlling the fiber using at least one electrically charged metallic disk rotating about an axis positioned below the needle; capturing the fiber using electrically grounded collector; extracting a single fiber branch thread from the polymer fiber streams, wherein the single fiber branch thread is attracted to and intercepted by the collector shape, and depositing the single fiber branch thread as substantially aligned fiber on the collector.

20 Claims, 14 Drawing Sheets

(56) References Cited

U.S. PATENT DOCUMENTS

| | | | |
|---|---|---|---|
| 2,123,992 | A | 7/1938 | Formhals |
| 2,187,306 | A | 1/1940 | Formhals |
| 2,349,950 | A | 5/1944 | Formhals |
| 6,106,913 | A | 8/2000 | Scardino et al. |
| 6,355,699 | B1 | 3/2002 | Vyakarnam et al. |
| 6,743,273 | B2 | 6/2004 | Chung et al. |
| 6,753,454 | B1 | 6/2004 | Smith et al. |
| 6,821,479 | B1 | 11/2004 | Smith et al. |
| 7,575,707 | B2 | 8/2009 | Xia |
| 7,828,539 | B1 | 11/2010 | Beachley et al. |
| 8,157,554 | B2 | 4/2012 | Petras et al. |
| 2002/0104606 | A1 | 8/2002 | Ohzuru et al. |
| 2005/0104606 | A1 | 5/2005 | Donsky |
| 2005/0137675 | A1 | 6/2005 | Dubson et al. |
| 2005/0224998 | A1 | 10/2005 | Andrady et al. |
| 2006/0226580 | A1 | 10/2006 | Xia et al. |
| 2007/0269481 | A1 | 11/2007 | Li et al. |
| 2007/0275458 | A1 | 11/2007 | Gouma |
| 2008/0170982 | A1 | 7/2008 | Zhang et al. |
| 2008/0241538 | A1* | 10/2008 | Lee .................. D01D 5/0076 428/401 |
| 2008/0290554 | A1 | 11/2008 | Wu et al. |
| 2009/0108503 | A1 | 4/2009 | Scott-Carnell et al. |
| 2009/0294733 | A1 | 12/2009 | Branham et al. |
| 2009/0324950 | A1 | 12/2009 | Kim |
| 2010/0197027 | A1 | 8/2010 | Zhang et al. |
| 2010/0327494 | A1* | 12/2010 | Jabbari ............... D01D 5/0076 264/466 |
| 2013/0273801 | A1 | 10/2013 | Young |
| 2014/0079759 | A1* | 3/2014 | Patel .................. A61L 27/50 424/443 |

FOREIGN PATENT DOCUMENTS

| | | |
|---|---|---|
| CN | 1776033 A | 5/2006 |
| EP | 2045375 A1 | 4/2009 |
| WO | 2004074559 A1 | 9/2004 |
| WO | 2005073442 A1 | 8/2005 |
| WO | 2005123995 A1 | 12/2005 |
| WO | WO2005123995 A1 | 12/2005 |
| WO | 2006052039 A1 | 5/2006 |
| WO | 2006135147 A1 | 12/2006 |
| WO | WO2009101472 A2 | 8/2009 |

OTHER PUBLICATIONS

Ali et al., "Electrospinning of Continuous Nanofiber Bundles and Twisted Nanofiber Yarns", Nanofibers—Production Properties and Functional Applications, 2011, pp. 153-174.

Li et al., "Electrospinning of Nanofibers: Reinventing the Wheel?**", Advanced Materials, 2004, vol. 16, No. 14, pp. 1151-1170.

Peterson, "Hybrid Nanomanufacturing Process for High-Rate Polymer Nanofiber Production", University of Nebraska—Lincoln, DigitalCommons@University of Nebraska—Lincoln, Engineering Mechanics Dissertations & Theses, 2010, 159 pages.

KdScientific, "Inflowmation Chronicles Highlights of Interesting Scientific Applications", Inflowmation Chronicles, Issue 1001, Spring 2009, 2 pages.

Theron et al., "Electrostatic field-assisted alignment of electrospun nanofibres", Nanotechnology, 12, 2001, pp. 384-390.

Tan et al., "Tensile testing of a single ultrafine polymeric fiber", Biomaterials 26, 2005, pp. 1453-1456.

Bashar Haseeb, "Controlled deposition and alignment of electrospun PMMA-g-PDMS nanofibers by novel electrospinning setups", Master of Science Thesis, KTH Chemical Science and Engineering, Stockholm, Sweden 2011, 164 pages.

Monika Rajput, "Optimization of Electrospinning Parameters to Fabricate Aligned Nanofibers for Neural Tissue Engineering", A Thesis Submitted in Partial Fulfillment of the Requirement for the Degree of Master of Technology in Biotechnology & Medical Engineering, Department of Biotechnology and Medical Engineering, National Institute of Technology, Rourkela, Orissa, India, 2012, 74 pages.

Neves et al., "Patterning of polymer nanofiber meshes by electrospinning for biomedical applications", International Journal of Nanomedicine, 2007, 2(3), pp. 433-448.

Theron A. et al., "Electrostatic field-assisted alignment of electrospun nanofibres", Nanotechnology 12, 2001, pp. 384-390.

Yee, W.A., et al., "Stress-induced structural changes in electrospun polyvinylidene difluoride nanofibers collected using a modified rotating disk," Polymer, 49, 2008, pp. 4196-4203.

Zussman E., et al.,"Assembly of Electronspun Nanofibers into Crossbars," Nanotechnology, Aug. 27, 2002, pp. 283-286.

Jianfeng Zhang, et al., "Preparation of biaxial orientation mats from single fibers," Advances in Polymer Technol., 2010, vol. 21, pp. 606-608.

Carnell, Lisa A., et al., "Aligned Mats from Electrospun Single Fibers", Macromolecules, vol. 41, No. 14, 2008, pp. 5345-5349.

Partial EP search report for corresponding EP15833663 dated Apr. 12, 2018.

* cited by examiner

```
90_deg_turn_program | Arduino 1.05
File Edit Sketch Tools Help

90_deg_turn_program
#include <Servo.h>
#define TURN_TIME 340

Servo myservo;

void setup()
{
    myservo.attach(10);

myservo.write(94);
} void loop()
{
    myservo.write(180);
    delay(TURN_TIME);
    myservo.write(94);
    delay(2000);
}
```

METHOD AND APPARATUS FOR CONTROLLED ALIGNMENT AND DEPOSITION OF BRANCHED ELECTROSPUN FIBER

CROSS REFERENCES TO RELATED APPLICATIONS

This application claims the benefit of U.S. Provisional Patent Application No. 62/038,506 filed on Aug. 18, 2014 in the name of Morshed Khandaker and William Paul Snow, which is expressly incorporated herein by reference in its entirety.

STATEMENT AS TO RIGHTS TO INVENTIONS MADE UNDER FEDERALLY SPONSORED RESEARCH OR DEVELOPMENT

This invention was made with government support under 8P20GM103447 awarded by the United States National Institutes of Health. The government has certain rights in the invention.

FIELD OF THE INVENTION

The present invention generally relates to the field of polymer fiber production. More specifically, the invention relates to the deposition of aligned fibers of micron to nano size diameters on different shapes of metallic implants and other types of substrates from a branched polymer during an electrospin process.

BACKGROUND OF THE INVENTION

The basic concept of electrostatic spinning (or electrospinning) a polymer to form extremely small diameter fibers was first patented by Anton Formhals (U.S. Pat. No. 1,975,504). Electrostatically spun fibers and nonwoven webs formed therefrom have traditionally found use in filtration applications, but have begun to gain attention in other industries, including in nonwoven textile applications as barrier fabrics, wipes, medical and pharmaceutical uses, and the like.

Electrospinning is a process by which electrostatic polymer fibers with micron to nanometer size diameters can be deposited on a substrate. Such fibers have a high surface area to volume ratio, which can improve the structural and functional properties of the substrate. Typically, a jet of polymer solution is driven from a highly positive charged metallic needle to the substrate which is typically grounded. Sessile and pendant droplets of polymer solutions may then acquire stable shapes when they are electrically charged by applying an electrical potential difference between the droplet and a flat plate. These stable shapes result only from equilibrium of the electric forces and surface tension in the cases of inviscid, Newtonian, and viscoelastic liquids. In liquids with a nonrelaxing elastic force, that force also affects the shapes. When a critical potential has been reached and any further increase will destroy the equilibrium, the liquid body acquires a conical shape referred to as the Taylor cone.

Naturally derived as well as synthetic polymers like collagen, gelatin, chitosan, poly (lactic acid) (PLA), poly (glycolic acid) (PGA), and poly(lactide-co-glycolide) (PLGA) have been used for electrospinning In addition to the chemical structure of the polymer, many parameters such as solution properties (e.g., viscosity, conductivity, surface tension, polymer molecular weight, dipole moment, and dielectric constant), process variables (e.g., flow rate, electric field strength, distance between the needle and collector, needle tip design, and collector geometry), and ambient conditions (e.g., temperature, humidity, and air velocity) can be manipulated to produce fibers with desired composition, shape, size, and thickness. Polymer solution viscosity and collector geometry are important factors determining the size and morphology of electrospun fibers. Below a critical solution viscosity, the accelerating jet from the tip of the capillary breaks into droplets as a result of surface tension. Above a critical viscosity, the repulsive force resulting from the induced charge distribution on the droplet overcomes the surface tension, the accelerating jet does not break up, and results in collection of fibers on the grounded target. Although the jet of fiber divides into many branches on its surface after the jet leaves the tip of the needle (Yarin, K Yarin, A. L., W. Kataphinan and D. H. Reneker (2005). "Branching in electrospinning of nanofibers." Journal of Applied Physics 98(6): —ataphinan et al. 2005). If not controlled, the branches of the fibers create a non-uniform deposition on the substrate. An objective of this invention is to enable control of deposition of branches of the fibers to provide uniform distribution of the fiber on a substrate.

Many engineering applications require uniform distribution of the fiber on the substrate. For example, one of the most important cell morphologies associated with tissue engineering is elongated unidirectional cell alignment. Many tissues such as nerve, skeletal and cardiac muscle, tendon, ligament, and blood vessels contain cells oriented in a highly aligned arrangement, thus it is desirable that scaffolds designed for these tissue types are able to induce aligned cell arrangements. It is well documented that cells adopt a linear orientation on aligned substrates such as grooves and fibers. Aligned nanofiber arrays can be fabricated using the electrospinning method [Li D, Xia Y. Electrospinning of nanofibers: reinventing the wheel? Adv Mater. 2004; 16:1151-1170] and many studies have shown that cells align with the direction of the fibers in these scaffolds.

In addition to the influence on fiber arrangement, cell alignment can have positive effects on cell growth within tissue engineering scaffolds. Myotubes formed on aligned nanofiber scaffolds were more than twice the length of myotubes grown on randomly oriented fibers (p<0.05) and neurites extending from DRG explants on highly aligned scaffolds were 16 and 20% longer than those grown on intermediate and randomly aligned scaffolds respectively [Choi J S, Lee S J, Christ G J, Atala A, Yoo J J. The influence of electrospun aligned poly(epsilon-caprolactone)/collagen nanofiber meshes on the formation of self-aligned skeletal muscle myotubes. Biomaterials. 2008 July; 29(19):2899-906].

Growth of electrical bending instability (also known as whipping instability) and further elongation of the jet may be accompanied with the jet branching and/or splitting. Branching of the jet of polymer during the electrospin process has been observed for many polymers, for example, polycaprolactone (PCL)(Yarin, Kataphinan et al. 2005), polyethylence oxide (Reneker, D. H., A. L. Yarin, H. Fong and S. Koombhongse (2000) "Bending instability of electrically charged liquid jets of polymer solutions in electrospinning" Journal of Applied physics 87(9): 4531-4547). Such branching produces non-uniform deposition of fiber on the collector during the electrospin process. A method and apparatus to separate out a continuous single thread of fiber from many fiber branches has not been solved. A method is needed by which uniformly distributed single thread fiber can be deposited on a substrate during electrospinning processes for various engineering applications requiring uniform, controlled fiber deposition on a substrate, including enabling elongated unidirectional cell alignment.

SUMMARY OF THE INVENTION

Micron to nano size fibers can be applied to a variety of substrates across a range of applications to enable or enhance desired performance. For example, when nano size fibers are fused with biomedical implants, osseointegration of an implant with the host tissue in orthopedics and orthodontics is improved. The effects of fibers on the interface fracture toughness of implant/cement specimens with and without fibers at the interface have not yet been known. Such studies are important for the design of a lasting implant for orthopedic applications. In one aspect, a specific goal of the present invention is to coat different orthopedic and orthodontic implants by aligned micron to nanosize fiber for the improvement of the bonding of the implant with the surrounding biomaterial in physiological conditions. In another aspect, the present invention can also be applied to catalysis, filtration media, filler for fiber-containing composites, and scaffolds for tissue engineering. Alignment of the electrospun fibers will increase the number of applications for which the fibers are suited, including for example, optical polarizers and bone scaffold matrix.

The present invention utilizes the lateral branching of fiber from the straight whipping jet of polymer to produce reduced diameter and aligned fiber on a collector compared to the straight whipping jet of fiber. The present invention utilizes the higher stretching distance from the origin of the branch to the collector (FIG. 2-31) to produce reduce diameter fiber compared to other methods (FIG. 2-30 and FIG. 2-33).

In accordance with certain embodiments of the present disclosure, a method and apparatus is provided to control the deposition of electrospun fiber width and alignment. The method includes significant modifications of current methods of electrospinning used to deposit micro fiber and nanofiber onto a substrate. Current methods and apparatus for electrospinning typically comprise four parts: syringe pump to control flow rate, syringe with a needle which act as one of the electrodes to charge the polymer solution, high-voltage power supply to generate electric field, and collector with substrate which acts as an electrode to collect fibers as illustrated in FIG. 1 (Khandaker, M., K. C. Utsaha and T. Morris (2014). "Interfacial fracture toughness of titanium-cement interfaces: Effects of fibers and loading angles." International Journal of Nanomedicine 9(1)). A polymer solution, sol-gel, particulate suspension or melt is loaded into the syringe and this liquid is extruded from the needle tip at a constant rate by a syringe pump. The collector is usually a charged parallel plate structure or some form of disk rotating in a plane perpendicular to the longitudinal axis of the syringe needle. Unlike current methods, the present invention can be used for not only non-woven polymer fabric or weaving polymer fibers into a fabric, but also on round, flat, and irregular (like hip implant, orthopedic screws) shape collectors. The present invention may also be used for metal coating with a controlled aligned fiber on these collectors. The present invention is configurable with multiple disks that provide a capability to adjust the length of spun fibers applied to a substrate, enabling parallel deposition of fibers across a range of substrate physical dimensions.

In the present invention, as illustrated in FIG. 2, FIG. 3 and FIG. 4, a syringe pump, syringe with a needle and a high-power electric power supply is used, however, instead of using a single rotating target disk or a pair of charged collector strips, a rotating auxiliary metallic disk is positioned in line with the syringe needle (as illustrated in FIG. 2), and configured having two insulating washers attached using a metallic fastener (e.g., bolt) adapted to engage a metal shaft. The fastener is electrically grounded. The sharp syringe needle is centered on the edge of the metallic disk substantially aligned with the plane of disk rotation. The needle is electrically positive charged. The path of an electromagnetic field generated by the potential difference between the charged needle and the rotating auxiliary metallic disk is used to deposit and align fiber on a primary collector shape. The primary collector shape rotates on an axis substantially orthogonal to the rotational axis of the auxiliary metallic disk. The invention uses the auxiliary metallic disk to pull away fibers from a fiber stream by applying an opposed charge to produce elongated unidirectional fibers. The opposed charge on the metallic disk and the charge on the needle may be generated by the high power voltage source.

Fiber directed towards the circumference of the primary collector shape may be utilized to deposit fiber on a relatively round or on flat substrates and other more irregular shapes (like hip implant shape or electrical substrates) that may be mounted on the primary collector shaft (as illustrated in FIG. 4). The primary collector shaft (as illustrated in FIG. 2) is set spinning by a DC motor and positioned to intercept an outer band fiber branches in the electromagnetic field, which coats the collector with aligned fiber. The position of the collector shape may be altered to move the axis of rotation toward or away from the fibers aligned with the electromagnetic field. The position of the needle may be adjusted using a non-conducting support (e.g., wooden or plastic bar) attached with the tube of the syringe to increase or decrease the distance between the needle tip and the edge of the metallic disk (as illustrated in FIG. 3). The needle, primary and auxiliary disk components can be mounted in a sealable chamber to avoid disturbance of the fiber flow due to the air flow from the room to the chamber. Using the present invention, an uninterrupted direct application of aligned fibers can be applied to a variety of target samples. The target samples may be any of a plurality of shapes, including those typical of biomedical implants, biomaterial interfaces and tissue engineering scaffolds. The insulating washers, fastener (e.g., bolt head) and primary collector shape (e.g., specimen holder) of the present invention are adaptable to achieve different coating topography (fiber diameter, distance between two fiber, coating thickness) on the target (e.g., an implant) surface. Research by the named inventors has shown (discussed in example section) that the applied coating of aligned fiber on an implant can induce and improve aligned cell arrangements, including elongated unidirectional cell alignment and the strength between implant/biomaterial interfaces. Further, the present invention is confirmed to enable control of the deposition of the branches of the fibers to provide uniform distribution of the fiber on the substrate.

In another embodiment, the present invention provides a dual disk method that incorporates the advantages of the electric field of the single disk method. The present invention is reconfigurable between a single disk and a multiple disk arrangement. Significant benefits of the two disk configuration are the ability to control the length of each fiber, rapidly collect parallel fibers of the same length, and the capability of single fiber collection. This is done similarly to the single disk collection method, but instead of attracting the fibers to the center the fibers are forced to the sharp edge of the disk. This is accomplished by taking advantage of the electromagnetic field of a thin solid disk near the edge. The field lines of a point charge both positive and negative produce the path of strongest attraction. The two rotating disks take advantage of the natural oscillation of the nanofiber, and in a manner similar to the parallel plate collection method. Giving the negatively charged disks the ability to rotate and tilt produces cross-linking (stray fibers) and the arcing effect of static charge respectfully. The fibers are allowed to follow random trajectories until they encounter the electro-magnetic field of the disk. At that point the fibers align back and forth along a plain that intersects both disks. The disks are mirrored and adjusted to the desired length, with both disks being negatively charged. Due to the fibers grounding out on the disk and sharing the same charge, along with the effects of the electro-magnetic field, there is an arcing effect. This effect is adjusted in shape by introducing a slight angle to both disks in opposite directions so the tops of the blades are closer together and the bottom of the disks are slightly further apart. Then by spinning the blades the fibers are pulled tight and one can collect the fibers with greater control. (See FIGS. 5a through 5d.)

BRIEF DESCRIPTION OF THE DRAWINGS

FIG. 5E is a non-limiting diagram showing a turn program created using Labview available from National Instruments Corporation.

DETAILED DESCRIPTION OF PREFERRED EMBODIMENTS OF THE INVENTION

Figure 1:
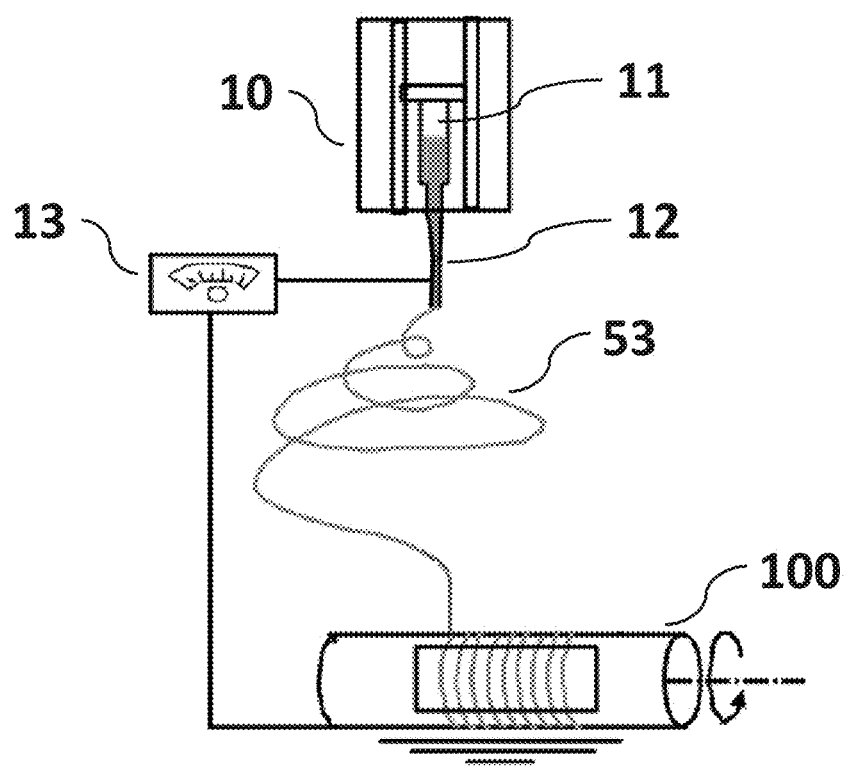
FIG. 1 is a non-limiting diagram showing a schematic view of typical laboratory setup for an Electrospinning process.

In brief:

FIG. 1 is a non-limiting diagram schematically illustrating the method of the typical electrospin process. A typical electrospin setup consists of syringe pump, syringe with a needle, high-voltage power supply, and collector. Presently a single rotating or flat target disk, a pair of charged collector strips have been used as the fiber collector.

Figure 2:
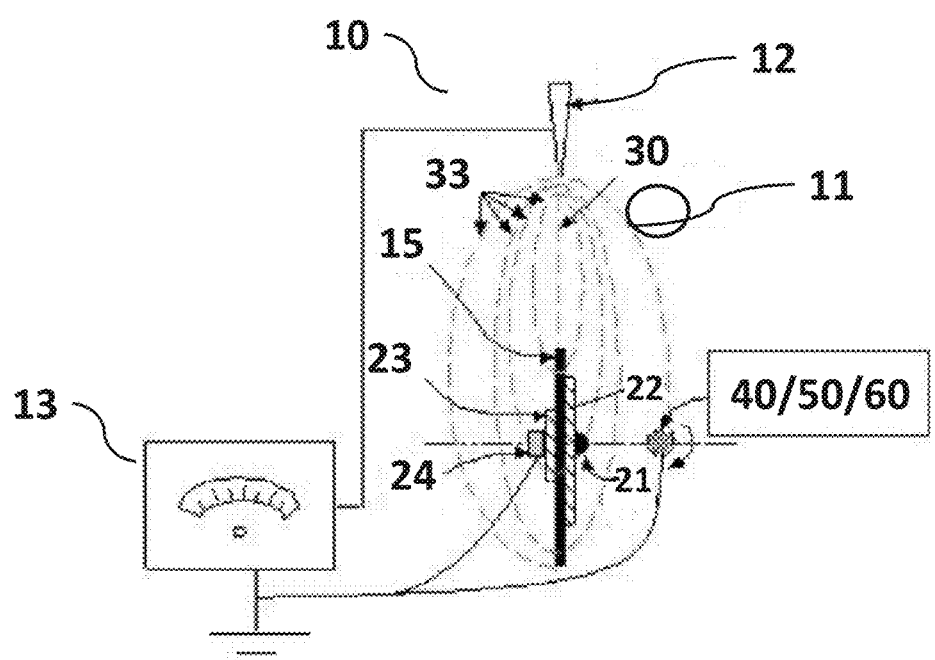
FIG. 2 is a non-limiting diagram showing a schematic view of the invention method.

FIG. 2 is a non-limiting diagram schematically illustrating the method of the present invention. The embodiment shown in the diagram uses the path of the electromagnetic field generated by the potential difference between charged needle and rotating auxiliary metallic disk using a high-power voltage source to capture, deposit and align fiber on a substrate. The apparatus shown includes the syringe needle, DC motor, blunt bolt, and front insulating washer. A linear stage is used to move the collector back and forth.

Figure 3:
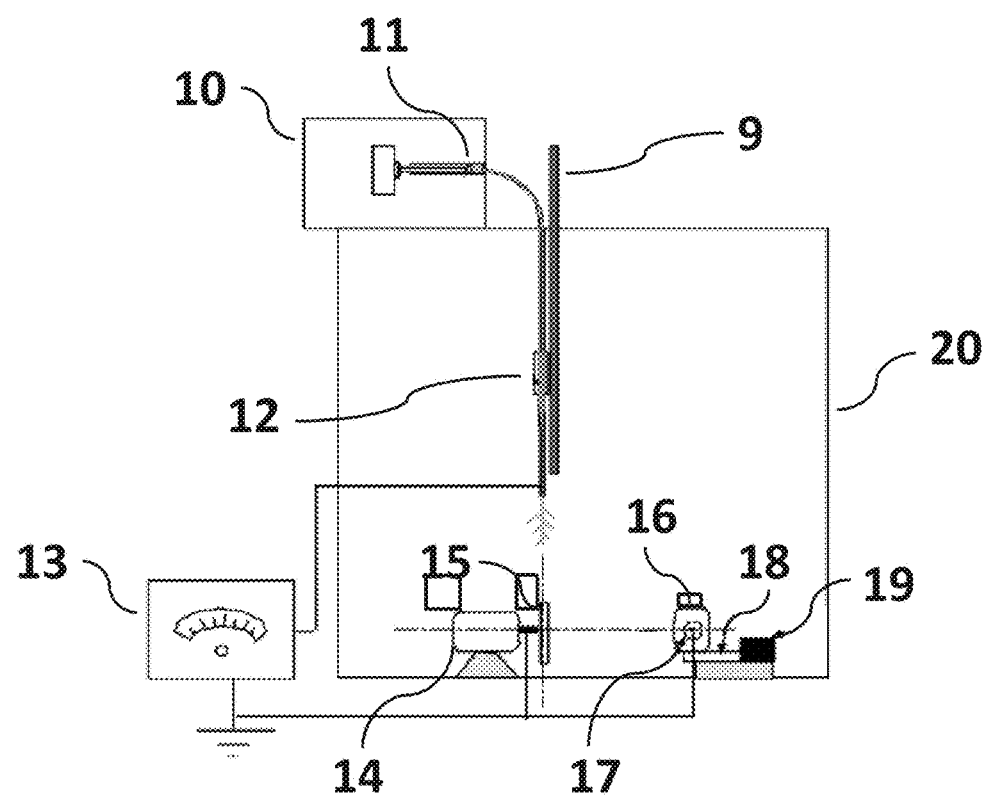
FIG. 3 is a non-limiting diagram showing components of the apparatus of the present invention.

FIG. 3 is a non-limiting diagram illustrating the components of the apparatus of the present invention. The embodiment shown in the diagram includes the sealable chamber, a syringe pump, a syringe with a tube that is attached using a non-conducting support, a syringe needle at the end of the tube, a high-voltage power supply, a rotating auxiliary metallic disk, and primary collector shapes. The metallic disk is positioned in line with the syringe needle. The metallic auxiliary disk and a primary collector shape are spun using direct current (DC) and speed controlled motors. The syringe needle is electrically charged by applying a high-voltage in the range of 5 KVA to 15 KVA produced by the power supply. An opposed charge is applied to the rotating disk by applying a high-voltage in the range of 5 KVA to 15 KVA generated by the power supply.

Figure 4:
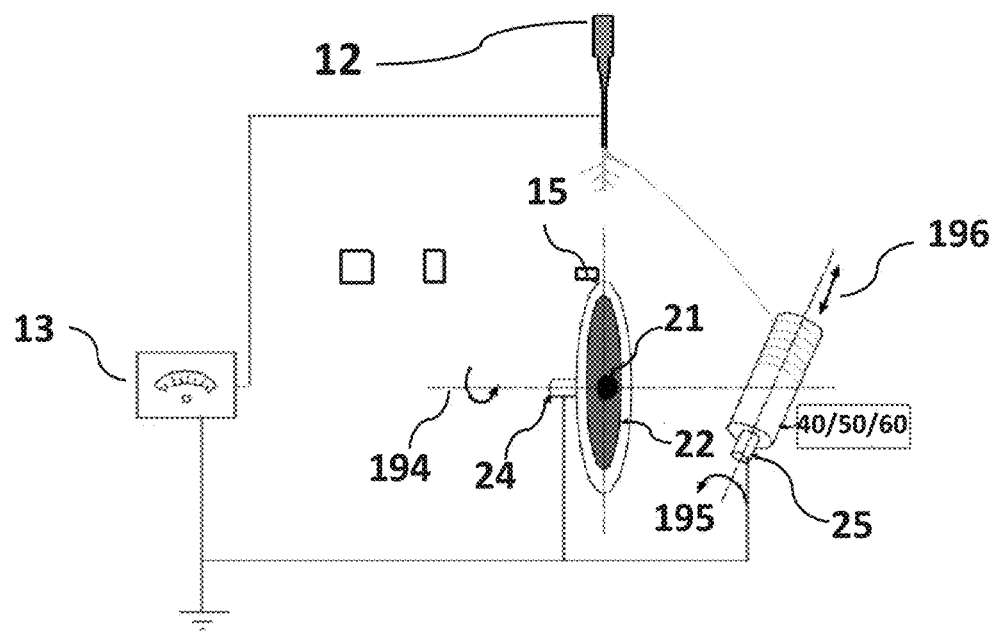
FIG. 4 is a non-limiting diagram showing the components of the apparatus of the present invention that is attached with primary and auxiliary disk.

FIG. 4 is a non-limiting diagram showing components of the apparatus of the present invention that is attached with primary and auxiliary disk. The embodiment shown in the diagram includes a syringe needle, an electric power supply, a rotating auxiliary metallic disk, and a primary collector shape. The metallic disk is positioned in line with the syringe needle, and configured having two insulating washers attached using a metallic fastener (e.g., bolt) adapted to engage (e.g., screwed into) with the motor shaft. The metallic bolt is grounded. The primary collector shape rotates on an axis substantially orthogonal to the rotational axis of the auxiliary metallic disk. The primary collector shape is grounded. The auxiliary metallic disk and the primary collector shape are spun using speed controlled, direct current (DC) motors.

Figure 5A:
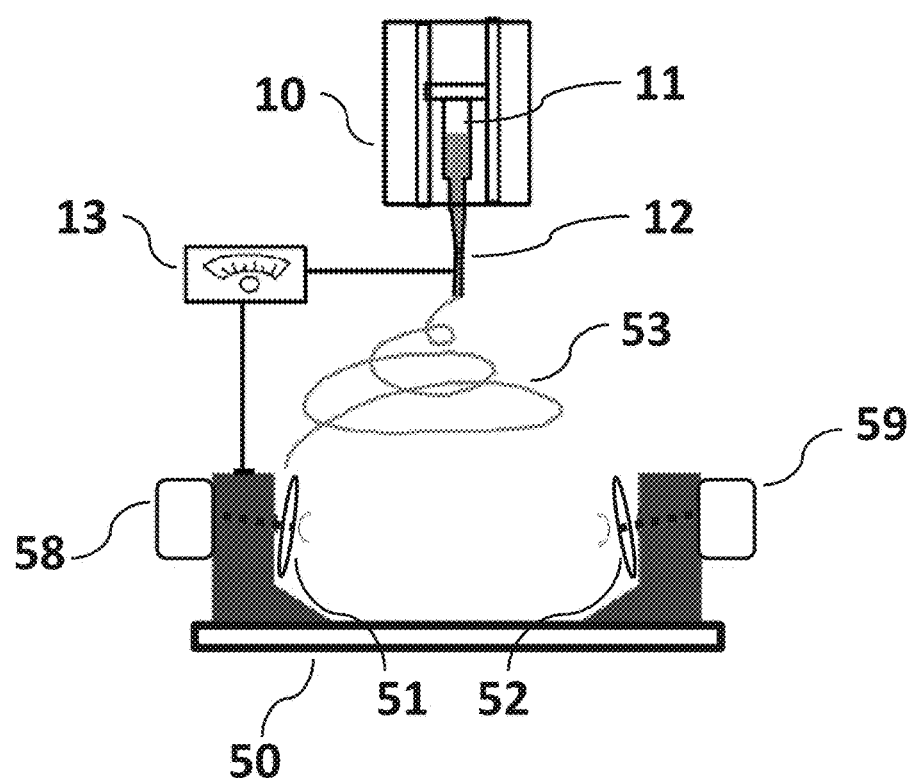
FIG. 5A is a non-limiting diagram showing a schematic view of the dual rotating disks configuration of the present invention that can be used to implement the method of controlling fiber alignment and deposition.

FIG. 5A is a non-limiting diagram showing a schematic view of the dual rotating disks configuration of the present invention that can be used to implement the method of controlling fiber alignment and deposition. The present invention provides a dual disk method that incorporates the advantages of the electric field of the single disk method.

Figure 5B:
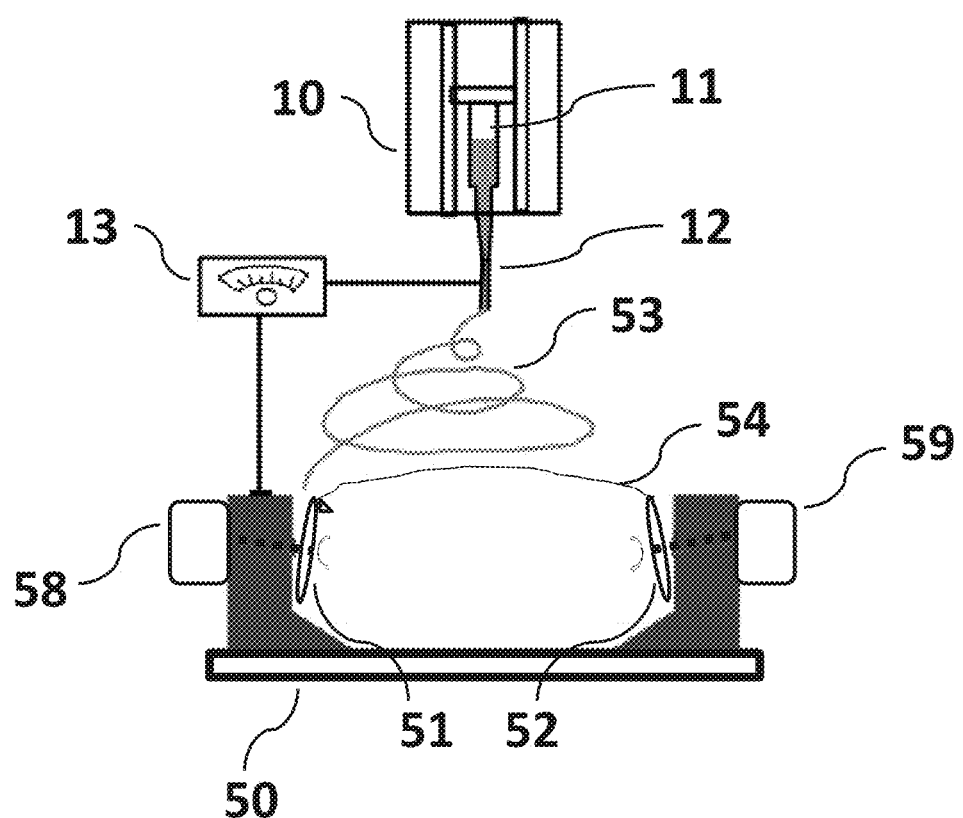
FIG. 5B is a non-limiting diagram showing how fiber control is accomplished similarly to the single disk collection method, but instead of attracting the fibers to the center of a single disk the fibers are forced to the sharp edge of the disk.

FIG. 5B is a non-limiting diagram showing how fiber control is accomplished similarly to the single disk collection method, but instead of attracting the fibers to the center of a single disk the fibers are forced to the sharp edge of the disk. The fibers are allowed to follow random trajectories until they encounter the electro-magnetic field of the disk.

Figure 5C:
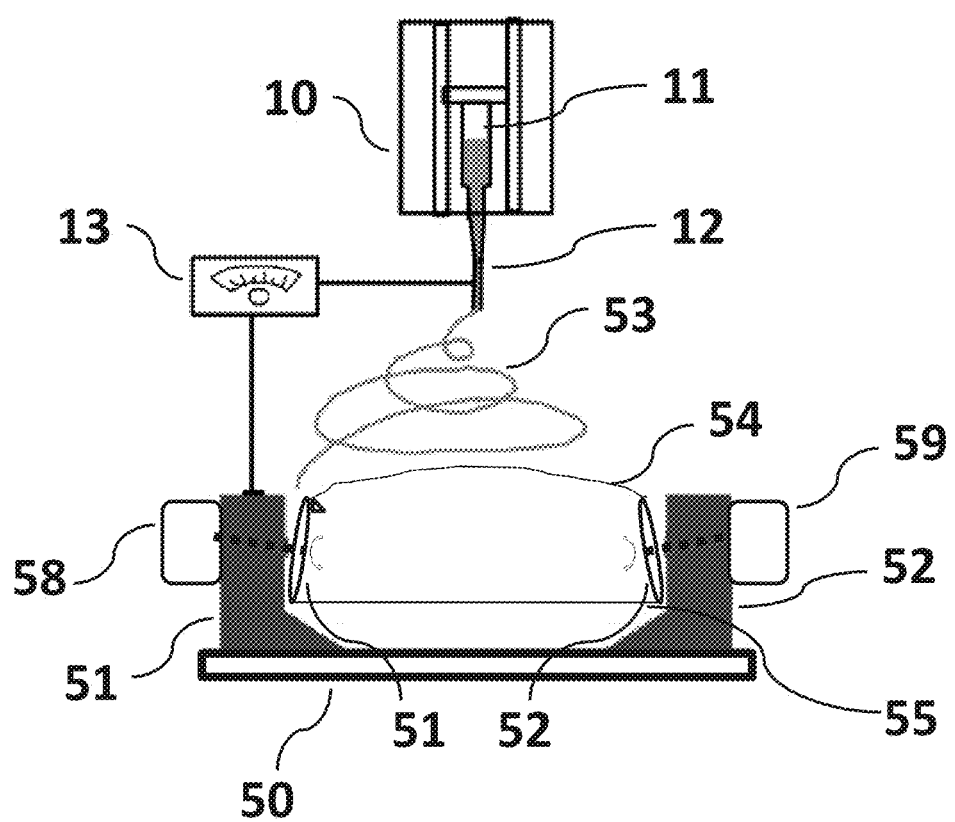
FIG. 5C is a non-limiting diagram showing the fibers pulled tight at the lower side of the disks where the fibers may be collected with greater control.

FIG. 5C is a non-limiting diagram showing the fibers pulled tight at the lower side of the disks where the fibers may be collected with greater control. Fiber length may be adjusted by increasing or decreasing the separation distance between the rotating disks.

Figure 5D:
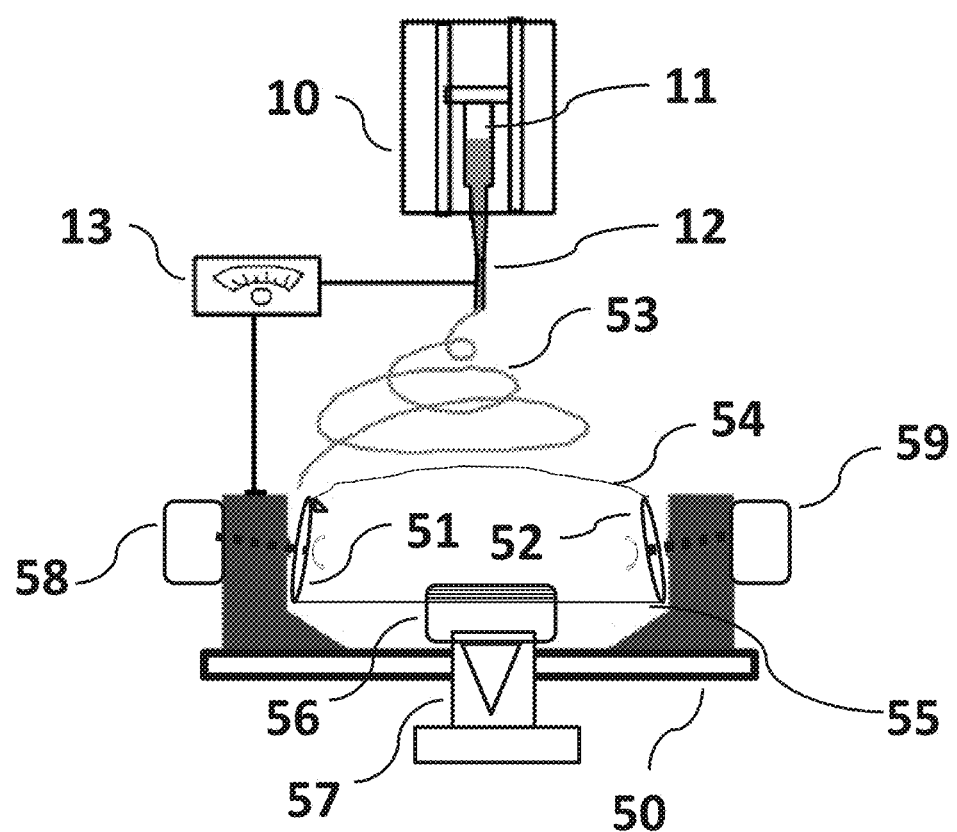
FIG. 5D is a non-limiting diagram showing a schematic view of the parallel rotating disks configuration of the present invention with a collection substrate positioned in the path of the fibers stretched between the rotating disks.

FIG. 5D is a non-limiting diagram showing a schematic view of the dual rotating disks configuration of the present invention with a collection substrate positioned in the path of the fibers stretched between the rotating disks. Once the fibers have been optimized a collection surface may be manipulated within the pathway of the stretched fibers.

FIG. 5E is a non-limiting diagram showing a turn program created using Labview available from National Instruments Corporation. To control the linear actuator motor a PWM (Pulse width modulation) circuit can be created. In developing the present invention the tool used to create the PWM was Labview.

Figure 6:
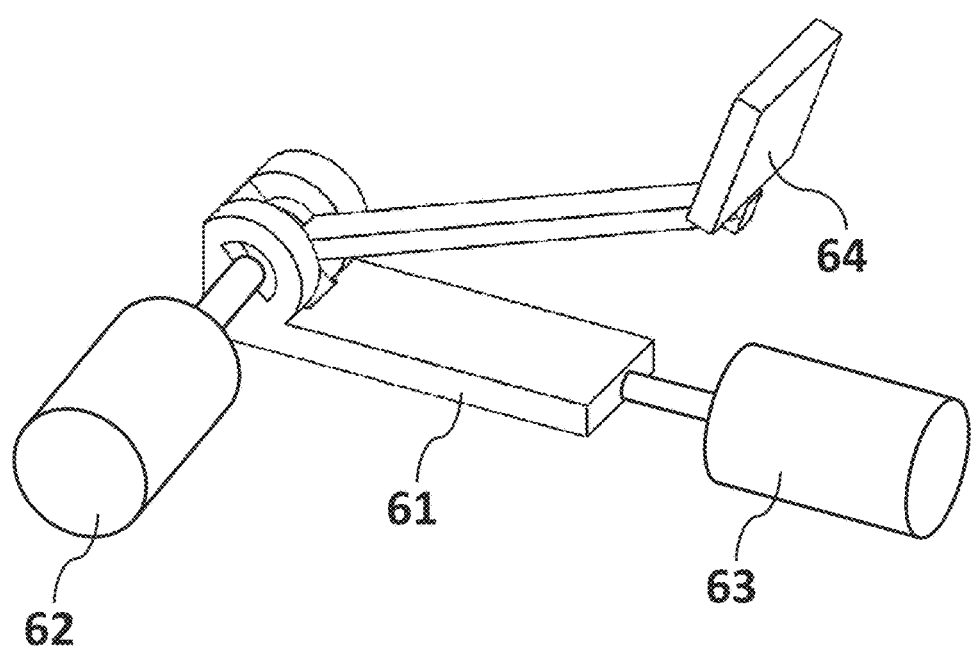
FIG. 6 is a non-limiting drawing showing an arm structure of the present invention that allows for single, parallel, and bidirectional (also known as scaffolding) fiber collection.
Figure 7:
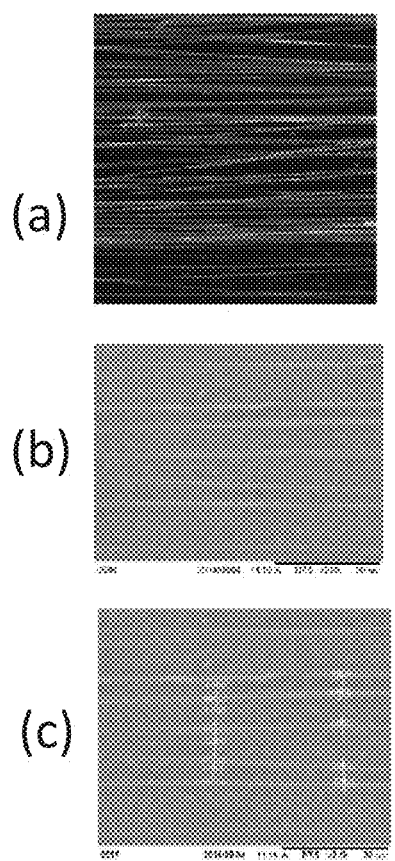
FIG. 7 is a non-limiting image that illustrates the controlled disposition of aligned fiber produced by the invention on round implant. (a) stereomicroscope image (8× magnification), (b) scanning electron microscope image (2000× magnification), (c) width and gap between adjacent fibers.
Figure 8:
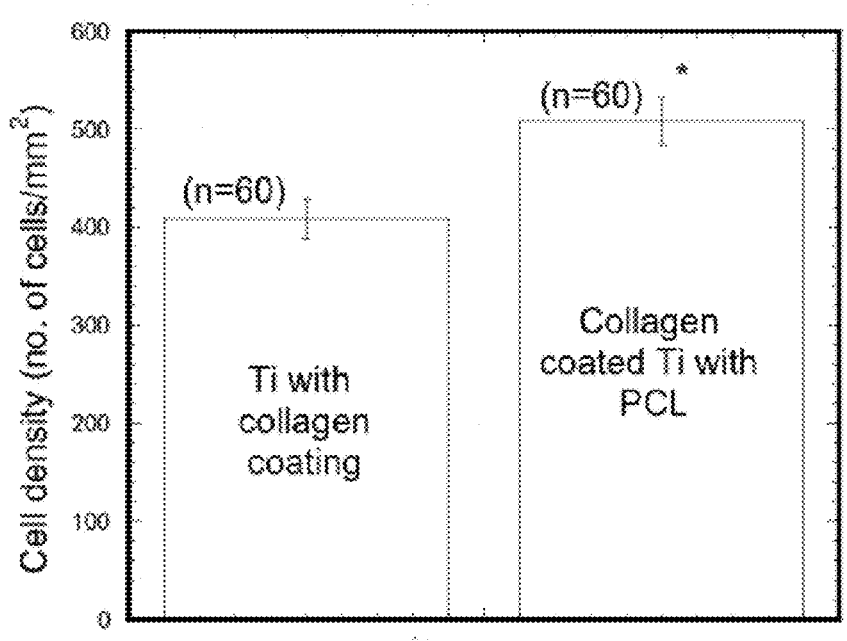
FIG. 8 is a non-limiting graph showing cell density on Ti samples after 2 weeks of cell culture.
Figure 9:
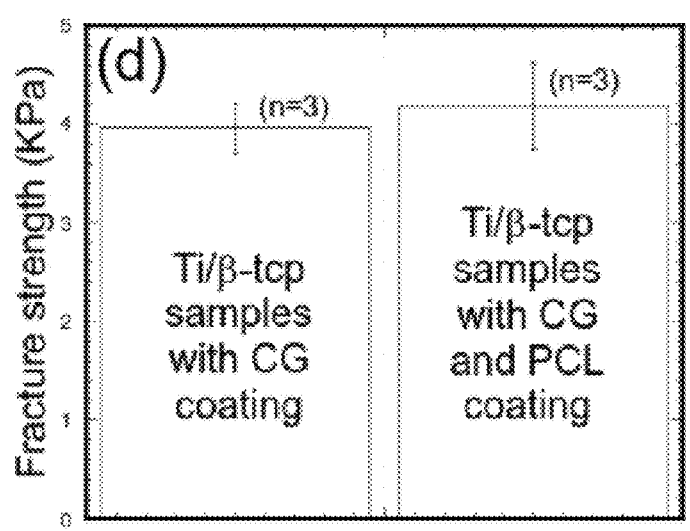
FIG. 9 is a non-limiting graph showing tensile test results of Ti/β-TCP samples.

FIG. 6 is a non-limiting drawing showing an arm structure of the present invention that allows for single, parallel, and bidirectional (also known as scaffolding) fiber collection. Actuating controls may be adapted for positioning the arm structure and controlling motion to capture aligned fibers with precise separation during deposition on a substrate. In detail:

Referring now to FIG. 2, a non-limiting diagram is shown schematically illustrating the single disk method of the present invention. The embodiment shown in the diagram uses the path of the electromagnetic field 33 generated by the potential difference between charged needle 12 and rotating auxiliary metallic disk 15 using a high-power voltage source 13 to capture, deposit and align fiber 31 on a substrate 40, 50, 60. The substrates 40, 50, and 60 may comprise relatively round 40 or irregular 50 or flat 60 shapes. A blunt headed bolt 21 may be used to attach two insulating washers 22 and 23 with the shaft of the motor. The auxiliary thin metallic disk 15 pulls away fibers by applying an opposed charge. The spinning primary collector shapes 40, 50, 60 intercept outer band fiber branch and coats a mounted shape 40, 50, 60 with aligned fibers. The diameter of the washers can be changed which may affect the amount of inside branches.

Referring now to FIG. 3, a non-limiting diagram illustrates components for the single disk configuration of the apparatus of the present invention. The electrospin chamber 20 housed the adjustable non-conducting support with the syringe needle 12, and the primary collector 17 and auxiliary disk 15. The embodiment shown in the diagram includes an infusion pump 10, syringe 11, syringe needle 12, an electric power supply 13, a rotating auxiliary metallic disk 15, and a primary collector shape 17. The metallic disk 15 is positioned in line with the syringe needle 12, and configured having two insulating washers (back washer is not shown, front washer is shown in FIG. 2, 22) attached using a metallic fastener (FIG. 2, 21), e.g., bolt adapted to engage (e.g., screwed into) a metal shaft (FIG. 2, 24). The metallic fastener is electrically grounded. The primary collector shape 17 rotates on an axis substantially orthogonal to the rotational axis of the auxiliary metallic disk 15. The metallic disk 15 and the primary collector shape 17 are spun using speed controlled, direct current (DC) motors 14 and 16. The syringe needle 12 is electrically charged by applying a high-voltage in the range of (5 KVA to 15 KVA) produced by the power supply 13. An opposed charge is applied to the rotating disk 15 by applying a high-voltage in the range of (5 KVA to 15 KVA) generated by the power supply 13. The axis of rotation for the collector shape 17 can be repositioned by moving adjusters using a linear stage 18, which is pushed back and forth by a linear actuator 19.

Referring now to FIG. 4, a non-limiting diagram shows in single disk configuration a schematic view of the invention method. The auxiliary metallic disk 15 configured having two insulating washers 22 and FIG. 2-23 attached using a metallic fastener (e.g., bolt) 21 adapted to engage (e.g., screwed into) a metal shaft 24. The metallic bolt 21 is electrically grounded. A primary collector shape 40 rotates on rotational axis 196 substantially orthogonal to the rotational axis 194 of the auxiliary metallic disk 15. The present invention uses the auxiliary metallic disk 15 to pull away fibers from fiber streams FIG. 2-30 and FIG. 2-33 by applying an opposed charge to produce elongated unidirectional fibers FIG. 2-31. The opposed charge on the metallic disk 15 and the charge on the needle 12 may be generated by the power supply 13. Fiber FIG. 2-31 directed towards the circumference of a primary collector shape 40 or 50 or 60 may be utilized to deposit a continuous single strand fiber FIG. 2-31 on a relatively round 40 or irregular 50 or flat 60 shapes that can be mounted on the shaft 25 of the speed control motor FIG. 3-16. The shaft 25 is electrically grounded. A primary collector shape 40 is fastened with the shaft of the speed control motor (FIG. 3-6) and positioned to intercept an outer band single strand fiber FIG. 2-31 in the electromagnetic field (shown as dashed lines FIG. 2), which coats the shapes with aligned fiber. The position of the collector shapes 40 or 50 or 60 may be altered to move the axis of rotation 196 toward or away from the plane of the electromagnetic field (dashed lines) using a linear stage FIG. 3-18 pushed back and forth by a linear actuator FIG. 3-19. The position of the syringe needle 12 may be adjusted to increase or decrease the distance between the needle tip and the edge of the metallic disk 15 by the non-conducting support (e.g., wooden or plastic bar) FIG. 3-9 that is fastened to the sealable chamber FIG. 3-20. The DC motor (FIG. 3, 14) may be used to spin the metallic disk 15 about its axis of rotation 194. Using the present invention, an uninterrupted direct application of aligned fibers can be applied to a variety of target samples mounted on the motor shaft 25. The target samples may be any of a plurality of shapes and structures, including those typical of biomedical implants, biomaterial interfaces and tissue engineering scaffolds. The insulating washers 22 and FIG. 2-23, fastener 21 (e.g., bolt head) and primary collector shape 17 (e.g., specimen holder) of the present invention is adaptable to achieve different coating topography on the target (e.g., an implant) surface mounted on the motor shaft 25, and control of the deposition of the branches of the fibers to provide uniform distribution of the fiber FIG. 2-31 on the collector shapes 40 or 50 or 60. The applied coat of aligned fiber on an implant can induce and improve aligned cell arrangements, including elongated unidirectional cell alignment.

Referring now to FIG. 5A, a non-limiting diagram shows a schematic view of the dual rotating disks configuration of the present invention that can be used to implement the method of controlling fiber alignment and deposition. The present invention provides a dual disk method, using a first disk 51 and a second disk 52 that incorporates the advantages of the electric field of the single disk method. The first disk 51 may be mounted on the rotational shaft of a first disk-speed control motor 58 and the second disk 52 may be mounted on the rotational shaft of a second disk-speed control motor 59. Benefits of configuring two disks 51 and 52 as in the present invention include a least the ability to control the length of each fiber, rapidly collect parallel fibers of the same length, and the capability of single fiber collection.

Referring now to FIG. 5B, fiber control is accomplished similarly to the single disk collection method, but instead of attracting the fibers 53 to the center of a single disk the fibers 53 are forced to the sharp edge of the disk (e.g. disk 51). This is accomplished by taking advantage of the electromagnetic field of a thin solid disk near the edge. The field lines of a point charge both positive and negative produce the path of strongest attraction. The two rotating disks 51 and 52 take advantage of the natural oscillation of the nanofiber 53, and in a manner similar to the parallel plate collection method. Giving the negatively charged disks the ability to rotate and tilt produces cross-linking (stray fibers) and the arcing effect of static charge, respectfully. The fibers 53 are allowed to follow random trajectories until they hit the electro-magnetic field of the disk (e.g., the first disk 51). At that point the fibers 54 align back and forth along a plain that intersects both disks. The disks 51 and 52 are mirrored and adjusted to capture fibers (FIG. 5C-55) of the desired length, with both disks 51 and 52 being negatively charged. Due to the fibers 53 grounding out on the first disk 51 and sharing the same charge, along with the effects of the electro-magnetic field, there is an arcing effect causing the fiber 54 to connect to the second disk 52. This effect is adjusted in shape by introducing a slight angle to both disks 51 and 52 in opposite directions so the tops of the disks 51 and 52 are closer together and the bottom of the disks 51 and 52 are slightly further apart, which stretches each connected fiber (FIG. 5C-55).

Referring now to FIG. 5C, by synchronized spinning of the disks 51 and 52 using the disk-speed control motors 58 and 59, the fibers 54 are pulled tight at the lower side of the disks 51 and 52 as stretched fibers 55, where the fibers 55 may be collected with greater control. Fiber-length may be adjusted by increasing or decreasing the linear separation distance between the first disk 51 and the second disk 52 by adjusting the separation position of the disk-speed control motors 58 and 59 on the base platform 50.

Referring now to FIG. 5D, a collection substrate 56 is shown positioned in the path of the fibers 55 stretched between the rotating disks 51 and 52. Once the fibers 54 have been optimized by stretching between the lower part of the disks 51 and 52, a collection shape 56 may be manipulated within the pathway of the stretched fibers 55. This can be done several different ways. The method with the most options would be implementing an arm structure 57 with variable control (angular, linear, along with extended rotational ability) as illustrated in FIG. 6. The arm structure 57 presented (see FIG. 6) allows for single, parallel, and bidirectional (also known as scaffolding) fiber collection. Scaffolding structures (non-woven) may be constructed by first placing the collection shape 56 in a first orientation in the pathway of the fibers 55 as shown in FIG. 5D. Multiple fibers may be collected as disks 51 and 52 are rotated by the disk-speed control motors 58 and 59, respectively, and the collection shape is incrementally repositioned by actuating controls (see FIG. 6) relative to path of the fibers 55. Subsequently, the collection shape 56 may be placed in a second orientation (e.g. rotated 90 degrees) in the pathway of the fibers 55. Multiple fibers may be collected as disks 51 and 52 are rotated by the disk-speed control motors 58 and 59, respectively, and the collection shape is incrementally repositioned by actuating controls (see FIG. 6). The second orientation may be achieved by rotating the collection shape substantially 90 degrees in the same plane with respect to the first orientation, producing a crossing pattern of fibers on the collection shape 56. Different crossing-patterns may be accomplished by varying the rotation angle. Multiple layers of fibers may also be collected and the crossing-patterns on the collection shape 56, controlled.

Referring now to FIG. 5E, a turn program 590 created using Labview is presented. To control the linear actuator motor a PWM (Pulse width modulation) circuit can be created. In developing the actuator controls for the present invention the tool used to create the PWM was Labview. A square signal was generated and transferred to a National Instruments Corp. (NI) tool called a MyDAQ. The MyDAQ transferred the signal to the PWM circuit enabling motor control. This paired with a linear actuating arm gave way to aligned fibers on a substrate that could be controlled very precisely. NI myDAQ combines hardware with eight ready-to-run software-defined instruments, including a function generator, oscilloscope, and digital multimeter (DMM); these software instruments are also used on the NI Educational Laboratory Virtual Instrumentation Suite II (NI ELVIS II) hardware platform. LabVIEW software can be combined with modular, reconfigurable hardware to produce precise actuator and motor control.

Referring now to FIG. 6, a non-limiting drawing shows an arm structure 61 of the present invention that allows for single, parallel, and bidirectional (also known as scaffolding) fiber collection. Actuating controls (62 and 63) may be adapted for positioning the arm structure 61. The arm structure 61 may be a fixed arm, include an arch stand, comprise belt stands, and incorporate rotating structural components. A fiber collection surface 64 may be rotationally mounted on the arm structure 61 as shown or in alternate positions. The arm structure 61 may be configured with at least one actuating control 62 or 63 to manipulate positioning of the structure for collecting fiber, including rotational positioning and linear positioning. Actuating controls 62 and 63 may be adapted for positioning a variety of structures and fiber collection substrates using industry standard motion control methods and processes directed to computer control of robotic instruments. For example, the motion may be controlled by a linear actuator, such as those available from Newport Corporation (model #LTA-HS) to produce aligned uni-direction fiber on a fiber collection surface 64. The fibers produced may be deposited on a collection surface 64 attached to the arm structure 61. r actuating arm gave way to aligned fibers on a substrate that could be controlled very precisely.

EXAMPLES

The present disclosure can be better understood with reference to the following non-limiting examples.
Aligned Fiber on Biomedical Implants The apparatus of the single disk configuration of the present invention for the control of the branching of fiber in an electrospin process is illustrated in FIG. 2 and FIG. 3. The invention as illustrated in FIG. 2 and FIG. 3 was used to configure an electrospinning unit to deposit aligned uni-direction polymer fibers on both a round hip implant and a flat sample material. Polycaprolactone (PCL), available from Sigma Aldrich, was selected as fiber material since it produces branches during Electrospinning process. PCL solution was prepared by ultrasonic (Sonics & Materials, Inc., Vibra-cell VCX 130) mixing of 7.69 wt % of PCL beads with acetone. The sonication process was carried out at approximately 80° C. for an hour. The solution was poured into a glass syringe in an infusion pump (Harvard Ins.).

A polymer solution was poured into a glass syringe in an infusion pump FIG. 3-10 for fiber production. Polymer was ejected from the glass syringe via a charged needle through a flexible tube. The needle FIG. 3-12 was charged by high voltage power source FIG. 3-13. The needle was attached with a wooden bar FIG. 3-9. The bar is attached with the sealable chamber FIG. 3-20 using a flexible adjusting clamp. The height of the needle can be adjusted by the wooden bar. A metallic saw blade FIG. 3-15 (referred to herein as auxiliary metallic disk) was positioned between two insulating washers FIG. 2-22 and FIG. 2-23. ABS plastic was the material used to produce the two insulating disks created using a 3D printer (Stratasys Inc., model—Dimension Elite). The metallic disc components were then spun on an aluminum shaft FIG. 3-24 via DC motor and held fastened by the grounding bolt.

A DC motor FIG. 3-16 was mounted on a precision linear stage (Newport Corporation, model#426). The motion of the stage was controlled by a linear actuator (Newport Corporation, model #LTA-HS) FIG. 3-19 to produce aligned uni-direction fiber on titanium rod fastened to the motor shaft. The fibers produced were deposited on a collector (not attached with the motor) which is fastened with the shaft. The auxiliary disk and implant was grounded and used in the electrospinning process for producing the aligned fibers shown in the micrograph presented in FIG. 7. As shown in the stereo FIG. 7(*a*) and scanning electron microscope FIG. 7(*b*) images, the present invention enables relatively precise collection of aligned fibers on a target sample. In a non-limiting example, a round rod is precisely moved to intercept the fiber path when it is spun. This interception and rotation causes a stripping of the fibers and results in alignment on the target sample. This interception point can be in several different locations with variable distances FIG. 7(*c*) with the method of interception varying with the equipment employed.

The electrospin process of the present invention was used for the deposition of aligned fiber on different shapes of titanium implants. The shapes of implants were round, hip, and flat shape implants. This process provides the capability of high precision for controlling deposition of the fibers and producing nano-level fibers. Each of the different kinds of implants was secured to their holders by different ways. A plurality of variable-shape holders was made using a 3D printer (Dimension elite 3D printer) in order to deposit aligned fiber on round hip implant and flat shape implants. Titanium (Ti) round and flat shape implants (6A1-4V ELI, ASTM B 348 standard, grade 23, biocompatible) available from Titanium Metal Supply, Inc., Poway, Calif. were used as implant materials. BioMet Inc. hip implant was used as hip shape implant. Round implant was secured on a cylinder shape holder using locknut. Hip implants were placed in the channel between the two pieces of hip implant holders and secured by a bolt and nut. Flat implants were glued on a hollow cylinder. The cylinder was press fitted on the flat shape implant holder. The selected implant holders ware press fitted on the shaft of the motor to deposit fiber on those implants. The implant was spun at high speed with a DC motor which was used in conjunction with a Probably Integral Derivative (PID) control system to control the revolutions of the motor under the electrospinning setup.

Cell Viability Tests to Find Fibers Effects on Biocompatibility of Ti

The effect of PCL and collagen (CG)-PCL coatings on Ti to the biocompatibility properties of Ti were examined. Three groups of Ti samples were prepared: (1) PCL coated Ti, (2) CG coated Ti (Ti/CG), and (3) CG and PCL coated Ti (Ti/CG/PCL). Ti surfaces were coated with thin layer of CG. Electrospun PCL fibers were randomly deposited on CG coated Ti to prepare Ti/CG/PCL samples. A custom made silicon well (FIG. 8*a*) was used to culture cells on each group of Ti surfaces. Mouse osteoblast cells (ATCC cell line # MT3T3E1) were seeded at a density of 5000 cells/ml on each well of Ti samples. Cells were cultured for 2 weeks on Ti samples in the well according to ATCC protocols. The cells were then fixed with neutral buffer formalin and stained with DAPI to identify nuclei. The resulting stain was viewed with a fluorescent microscope. The quantitatively and qualitatively measurement of cell viability on the Ti surfaces were conducted from the captured images. The study found negligible cell attachment and proliferation on only PCL coated Ti. Cells proliferate successfully on the surface of Ti/CG and Ti/CG/PCL samples. Cells grew along the fiber direction on Ti/CG/PCL surfaces with increased cell clustered along the fibers. Cell densities of Ti/CG/PCL samples were significantly higher compare to Ti/CG samples (FIG. 8*b*). These results suggested that PCL fiber positively influence the osseointegration of Ti surface that may lead to enhance in vitro and in vivo mechanical integration of Ti/bone interfaces.

In Vitro Tests to Evaluate PCL Fiber Effect on Ti/Bone Interfaces

The influence of the osseointegration on the bonding strength, $\sigma t$, between Ti and bone scaffold due to CG and CG/PCL fiber coatings on Ti were examined. Beta tricalcium phosphate (β-TCP) (3D Biotek, LLC, NJ) disk (9.5 mm diameter×1.6 mm thickness) was used as bone scaffold. Cells were cultured on the top of Ti, Ti/CG, Ti/CG/PCL and β-TCP surfaces for 14 days. β-TCP were placed on top of Ti/CG and Ti/CG/PCL specimen in a custom made acrylic well to make the coupled β-TCP-Ti/CG and β-TCP-Ti/CG/PCL specimen. A set of weights was placed on the samples via acrylic rod to avoid any displacement of the samples during cell culturing for 2 months. The coupled samples were glued on the holders in the Evex tensile test stage. Tension tests were conducted at strain rate 0.001 mm/sec to determine the $\sigma t$ values of the samples. We have found that no bonding between Ti and β-TCP whereas Ti/β-TCP samples with CG and CG-PCL showed noticeable bonding strength, $\sigma t$, though the differences of $\sigma t$ between those samples were not significant. This result suggested that both CG and CG-PCL can improve the bonding of Ti/bone. Further in vitro and in vivo improvement of Ti/bone union is possible by aligned, uniform and less stiff fiber on Ti using PCL nanofibers and MgO nanoparticles that is sought in future study.

Aligned Fiber Applications Using the Present Invention

Figure 10:
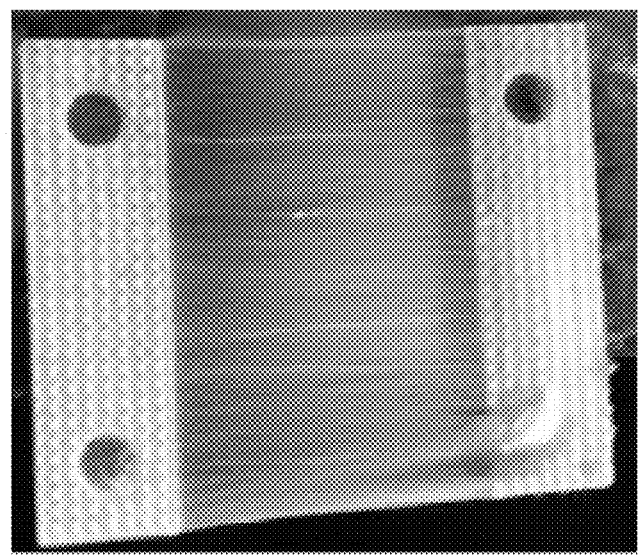
FIG. 10 is a non-limiting image showing aligned fiber between two parallel plates.

The single disk configuration disclosed for the present invention may be used for precision deposition of fiber on parallel surfaces as shown in FIG. 10. This was done by negatively charging the parallel plates and attaching them on a linear stage. The electro spun fibers reacted to the electric field and aligned along the field lines between both plates. This arrangement was used to test the tensile strength of the fibers produced which shows super plastic behavior of the aligned fiber strip.

Aligned Fiber Applications Using the Dual Disk Method of the Present Invention

The dual disk configuration of the present invention evolved from using the single disk setup into a new concept advanced from the knowledge gained from trial and error. The invention progressed from basic parallel plates, to a variation/blend of parallel plates and sharp blade, then ending with a completely new technique for achieving electrospun alignment. This new technique is a combination of parallel/drum/and sharp blade setups or PRD (Parallel Rotating Disks).

The specific setup for the dual disk configuration is dependent on the chemical solution being used to produce fibers. Factors such as viscosity, chemical makeup, and viscoelastic conditions dictate the tilt, speed, and voltage required to effectively electrospin the fibers. A solution customization process is used to optimize the collection of aligned fibers. This process is:

1. Determine the desired length of fiber.
2. Set blade stands to accommodate length from number 1.
3. Understand the viscoelastic relationship as it relates to surface tension.
4. Adjust the height of the needle to allow a sufficient room for the Taylor cone and fiber plumb to form.
5. The voltage should start low and slowly be increased until the Plumb is wide enough to accomplish the desired length of the fiber on the blade.
6. Once the fibers start to collect on the blade adjust the tilt to eliminate the arcing due to residual electric charge.
7. Depending on application the rotation of the blades can be slowly increased to the desired speed.

Once the fibers have been optimized a collection surface may be positioned in the pathway of the fibers (See FIG. 5d). This can be done several different ways. The method with the most options was found to be an arm with variable control (angular, linear, along with extended rotational ability). The arm presented in FIG. 7 allows for single, parallel, and bidirectional (also known as scaffolding) fiber collection, and includes rotational components for changing position of a substrate. Other methods considered and tested include a fixed arm, arch stand, and belt stands.

Example Applications for Use of the Present Invention

Nanofiber scaffolding structures and aligned fibers produced using the apparatus and methods of the present invention have applications in medicine, including artificial organ components, tissue engineering, implant material, drug delivery, wound dressing, and medical textile materials. Nanofiber scaffolding structures may be used to fight against the HIV-1 virus, and be able to be used as a contraceptive. In wound healing, nanofiber scaffolding structures assemble at the injury site and stay put, drawing the body's own growth factors to the injury site. These growth factors comprise naturally occurring substances such as proteins and steroid hormones capable of stimulating cellular growth, proliferation, healing, and cellular differentiation. Growth factors are important for regulating a variety of cellular processes. Scaffolding structures produced by the present invention and methods may be used to deliver medication to a wound site.

Protective materials incorporating nanofibers produced by the present invention and methods may include sound absorption materials, protective clothing directed against chemical and biological warfare agents, and sensor applications for detecting chemical agents. Gloves incorporating aligned fibers and scaffolding structures produced by the apparatus and methods of the present invention may be configured to provide persistent anti-bacterial properties. Applications in the textile industry include sport apparel, sport shoes, climbing, rainwear, outerwear garments, and baby-diapers. Napkins with nanofibers may contain antibodies against numerous biohazards and chemicals that signal by changing color (potentially useful in identifying bacteria in kitchens).

Filtration system applications include HVAC system filters, ULPA filters, air, oil, fuel filters for automotive, trucking, and aircraft uses, as well as filters for beverage, pharmacy, medical applications. Applications include filter media for new air and liquid filtration applications, such as vacuum cleaners. Scaffolding structures produced by the apparatus and methods of the present invention enable high-efficiency particulate arrestance or HEPA type of air filters, and may be used in re-breathing devices enabling recycling of air. Filters meeting the HEPA standard have many applications, including use in medical facilities, automobiles, aircraft and homes. The filter must satisfy certain standards of efficiency such as those set by the United States Department of Energy (DOE).

Energy applications for aligned fibers and scaffold structures produced using the apparatus and methods of the present invention include Li-ion batteries, photovoltaic cells, membrane fuel cells, and dye-sensitized solar cells. Other applications include micropower to operate personal electronic devices via piezoelectric nanofibers woven into clothing, carrier materials for various catalysts, and photocatalytic air/water purification.

In one aspect, using the method and apparatus of the present invention, aligned fibers may be arranged in a similar orientation as ligament. The aligned fibers can be collected in several rows and then spun into a thread, which would be usable as a ligament. The invention implemented for this application may be configured as a portable device, where a clinician in a hospital setting could use the aligned fiber to make skin like sutures.

In another aspect, using the method and apparatus of the present invention, aligned fibers may be applied to a substrate comprising a strip of paper, fabric, or tissue. Further heat treatment can be applied to melt the fibers to produce a very strong bond with the substrate. The bonded material could then be used as a healing "bandaid" to protect a wound and promote cell growth. Engineered tissue cells or nanomedicine will be attached to the pad and the "bandaid" applied to allow it to protect while it reacts with the white blood cells to bond and deliver medication.

In another aspect, aligned fibers produced using the method and apparatus of the present invention may be applied as a coating over electrostatic polymer to improve the electrical properties of polymer. The coated polymer could then be used to make artificial nerves for cochlear implants that could carry the electrical signals. The aligned fibers may also be used to enclose soft hydrogel to make intervertebral disk implant.

In another aspect, using the method and apparatus of the present invention, aligned fibers may be arranged in a scaffold like structure and then coated or covered with a flexible bonding material where the combined product is layered on to a damaged surface as a repair or other purpose such as enabling a heating layer when a electric current is applied to the fiber.

In another aspect, using the method and apparatus of the present invention, aligned fibers may be arranged in a scaffold structure where the spacing between fibers is adjusted to achieve a substantially specific numerical value to create a filter material having a defined porosity.

The apparatus of the present invention may be configured as a portable device movable between user locations to produce and align fiber on a substrate for a specific purpose.

The apparatus of the present invention may be configured as a stand-alone device integrated into a laboratory environment to produce and align fiber on a substrate for a plurality of research purposes.

The apparatus of the present invention may be configured as a stand-alone manufacturing device for producing products incorporating aligned fiber.

The apparatus of the present invention may be configured with a single disk or multiple disks, and may be reconfigured from one arrangement to the other as required by a specific application. The apparatus of the present invention may be implemented in a plurality of physical enclosure configurations to produce and align fiber on a substrate for a specific purpose or a variety of applications. Auxiliary functions may be incorporated into the physical enclosure and include at least any of ventilation, heating, cooling, illumination, electric power interface and computer aided controls and associated programming. The enclosure may be sealable.

The apparatus of the present invention may be configured as part of a manufacturing process scaled to produce a relatively high volume of products incorporating aligned fiber. The scaled up manufacturing process may comprise multiple instances of the apparatus of the present invention. The apparatus may be configured in a plurality of sizes ranging from smaller scale machines suitable for low volume production to larger size machines suitable for larger volume production of products incorporating nanofibers. The machines sized in any scale may incorporate single disk or multiple disks configurations, and may be reconfigurable.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. An apparatus for separating out a continuous single thread of fiber from many fiber branches consisting essentially of:
    a holder to support and rotate an electrically grounded collector shape about a first axis;
    a single metallic disk that can be rotated about a second axis;
    two insulating washers covering the surfaces of said single metallic disk and leaving a sharp circumferential edge exposed, said washers being attached to said single metallic disk using a metallic fastener adapted to engage a metal shaft, said metallic fastener being electrically grounded;
    an electrically chargeable syringe needle for electrospinning synthetic polymer fiber streams, said syringe needle tip positioned substantially in line with a circumferential edge of said single metallic disk;
    a linear stage to position said collector shape to engage a portion of an electromagnetic field generated by an electrical potential difference between said syringe needle and the circumferential edge of said single metallic disk, and
    a high voltage power supply for applying an opposed electrical charge to at least said syringe needle,
    wherein said electromagnetic field is shaped to pull branch fibers within said polymer fiber streams away from said streams, and
    wherein, said collector shape is continuously rotated to circumferentially collect single fiber branch thread directly from said electromagnetic field.

2. The apparatus of claim 1, wherein single fiber branch thread is extracted from said polymer fiber streams by positioning said collector shape to intercept said branch thread, said collector shape being continuously rotated around said first axis and said first axis positioned at one of an orthogonal or oblique angle relative to said second axis.

3. The apparatus of claim 1, wherein said single fiber branch thread is intercepted by said collector shape positionally adjusted by said linear stage to form layers of branch fiber thread wound spirally around said collector shape.

4. The apparatus of claim 1, wherein said single fiber branch thread is deposited as substantially aligned fiber on said collector shape.

5. The apparatus of claim 4, wherein said collector shape is one of a temporary product fabrication support, a filter fabrication frame, an electrical substrate, a biomedical implant or a foundation for constructing a tissue engineering scaffold.

6. The apparatus of claim 5, wherein the biomedical implant is one of a hip implant or a dental implant.

7. An apparatus for separating out a continuous single thread of fiber from many fiber branches consisting essentially of:
    a holder to support and rotate an electrically grounded collector shape about a first axis;
    a single disk that can be rotated on a shaft about a second axis substantially orthogonal to said first axis, said single disk being adapted to accept an electrical charge;
    an insulating medium attached to and covering the surfaces of said single disk leaving an uncovered circumferential sharp edge and a connector adapted to engage said shaft, said connector being electrically grounded;
    an electrically chargeable syringe needle for electrospinning fiber streams, said syringe needle having a tip positioned substantially in line with said single disk;
    a linear stage to position said collector shape to engage a portion of an electromagnetic field generated by an electrical potential difference between said syringe needle and a circumferential edge of said single disk, said fiber streams comprising branch threads generally aligned with said electromagnetic field; and
    a high voltage power supply for applying an electrical charge to at least said syringe needle,
    wherein, said collector shape is continuously rotated around said first axis to circumferentially collect single fiber branch thread directly from said electromagnetic field.

8. The apparatus of claim 7, wherein said collector shape is positioned to extract single fiber thread from said fiber streams.

9. The apparatus of claim 8, wherein said collector shape is dynamically positionable to intercept said single fiber thread forming spiral patterns around said collector shape.

10. The apparatus of claim 8, wherein said single branch fiber thread is deposited as a plurality of substantially aligned fibers on said collector shape.

11. The apparatus of claim 10, wherein said collector shape is one of a temporary product fabrication support, a filter fabrication frame, an electrical substrate, a biomedical implant or a foundation for constructing a tissue engineering scaffold.

12. The apparatus of claim 11, wherein said biomedical implant is one of a hip implant or a dental implant.

13. The apparatus of claim 7, further adapted to alter positioning of said collector shape to move the axis of rotation toward or away from said fibers aligned with said electromagnetic field.

14. The apparatus of claim 13, wherein said collector shape is adapted to intercept fibers in an outer band of said electromagnetic field.

15. The apparatus of claim 7, further adapted to alter positioning of said needle using a non-conducting support to increase or decrease separation between said needle tip and the edge of said single disk.

16. An apparatus for separating out a continuous single thread of fiber from many fiber branches, consisting essentially of:
    a holder to support and rotate an electrically grounded collector shape about a first axis;
    a single, electrically chargeable disk that can be rotated on a shaft about a second axis;
    an electrically grounded connector adapted to engage said shaft;
    an electrically chargeable syringe needle for electrospinning fiber streams, said syringe needle having a tip positioned substantially in line with said single disk realizing an electrical potential difference;
    a first drive unit for rotating said electrically grounded collector shape about said first axis, said first drive unit adapted to variously position said collector at oblique angles relative to said second axis;
    a power source for applying an electrical charge to said single disk;
    a second drive unit for rotating said single disk on said shaft about said second axis;
    a power source for electrically charging said syringe needle;
    wherein said holder is adapted to position said collector shape in a portion of an electromagnetic field generated by said potential difference between said syringe needle and an edge of said single disk, said fiber streams comprising threads generally aligned with said electromagnetic field;
    wherein said collector shape is adapted to intercept at least one single branch thread from said fiber streams, and wherein, said at least one single fiber branch thread is wound circumferentially around said rotating collector shape.

17. The apparatus of claim 16, wherein said first drive unit is adapted to alter positioning of said collector shape to move the axis of rotation toward or away from said fibers aligned with said electromagnetic field.

18. The apparatus of claim 17, wherein said collector shape is adapted to collect multiple layers of aligned fiber.

19. The apparatus of claim 16, wherein said collector shape is one of a temporary product fabrication support, a filter fabrication frame, an electrical substrate, a biomedical implant, or a foundation for constructing a tissue engineering scaffold.

20. The apparatus of claim 19, wherein said biomedical implant is one of a hip implant or a dental implant.

* * * * *